United States Patent
Chang et al.

(10) Patent No.: US 12,345,679 B2
(45) Date of Patent: Jul. 1, 2025

(54) SELF-POWERED FORMALDEHYDE SENSING DEVICE

(71) Applicant: National Taiwan University of Science and Technology, Taipei (TW)

(72) Inventors: Chih-Yu Chang, Taipei (TW); Chun-Yi Ho, Taipei (TW); Yu-Hsuan Cheng, Taipei (TW); Ying-Ying Chen, Taipei (TW)

(73) Assignee: National Taiwan University of Science and Technology, Taipei (TW)

( * ) Notice: Subject to any disclaimer, the term of this patent is extended or adjusted under 35 U.S.C. 154(b) by 413 days.

(21) Appl. No.: 18/069,593

(22) Filed: Dec. 21, 2022

(65) Prior Publication Data

US 2024/0085369 A1    Mar. 14, 2024

(30) Foreign Application Priority Data

Sep. 12, 2022   (TW) .................................. 111134386

(51) Int. Cl.
| | |
|---|---|
| *G01N 27/416* | (2006.01) |
| *G01N 27/30* | (2006.01) |
| *H02N 1/04* | (2006.01) |

(52) U.S. Cl.
CPC ........... *G01N 27/416* (2013.01); *G01N 27/30* (2013.01); *H02N 1/04* (2013.01)

(58) Field of Classification Search
CPC .. G01N 27/416; G01N 27/30; G01N 33/4975; G01N 33/497; G01N 27/60; H02N 1/04
See application file for complete search history.

(56) References Cited

U.S. PATENT DOCUMENTS

2013/0032160 A1*  2/2013  Bromberg .............. B01J 20/226
                                                        131/334
2018/0178191 A1*  6/2018  Schwab ..................... C08J 5/18

OTHER PUBLICATIONS

Lin et al., "A Self-Powered Triboelectric Nanosensor for Mercury Ion Detection," 2013, Angew. Chem. Int. Ed., vol. 52, pp. 5065-5069 (Year: 2013).*
Su et al., "Alveolus-Inspired Active Membrane Sensors for Self-Powered Wearable Chemical Sensing and Breath Analysis," 2020, ACS Nano, vol. 14, pp. 6067-6075 (Year: 2020).*

(Continued)

*Primary Examiner* — Luan V Van
*Assistant Examiner* — Kaylee Tseng
(74) *Attorney, Agent, or Firm* — Millen, White, Zelano & Branigan P.C.; William F. Nixon (57) ABSTRACT

Disclosed is a self-powered formaldehyde sensing device, comprising: a triboelectric material electrode layer including a first substrate and a first electrode layer formed on the first substrate; a triboelectric material dielectric layer including a second substrate, a second electrode layer formed on the second substrate, a dielectric reacting layer formed on the second electrode layer, and a reaction modification layer formed on the dielectric reacting layer to surface-modify the dielectric reacting layer, the reaction modification layer being a phosphomolybdic acid complex (cPMA) layer, the phosphomolybdic acid complex of the phosphomolybdic acid complex layer being obtained by dissolving 4,4'-bipyridine (BPY) in isopropanol (IPA) and then mixing with phosphomolybdic acid (PMA) solution; an elastic spacer; and an external circuit.

12 Claims, 9 Drawing Sheets

(56) References Cited

OTHER PUBLICATIONS

Wang et al., "Ultrasensitive flexible self-powered ammonia sensor based on triboelectric nanogenerator at room temperature," 2018, Nano Energy, vol. 51, pp. 231-240 (Year: 2018).*

* cited by examiner

SELF-POWERED FORMALDEHYDE SENSING DEVICE

FIELD OF THE INVENTION

The present invention relates to a formaldehyde sensing device, and more particularly relates to a self-powered formaldehyde sensing device.

BACKGROUND OF THE INVENTION

Lung cancer is the cancer with the highest morbidity and mortality worldwide. Screening, early diagnosis and early treatment are effective ways to reduce the lung cancer mortality. Among the conventional screening measures, breath diagnosis is a kind of promising screening measure which combines high quickness, non-invasiveness and high sampling convenience to assist in diagnosing what kind of disease a patient suffers by detecting volatile organic compounds (VOCs) exhaled from the human body. Formaldehyde is regarded as one of the biomarkers of lung cancer, and thus the early detection, disease course prediction and prognosis management of lung cancer can be carried out by the breath diagnosis.

Currently known related instruments capable of detecting formaldehyde have the following disadvantages: expensive, bulky and heavy, and the detection time is too long. In addition, a conventional formaldehyde sensing device also has many disadvantages, such as the need to rely on external power supply to operate, the need to detect at high temperatures, slow response time and lack of portability, which severely limit the practical application of the formaldehyde sensing device in the early diagnosis of lung cancer.

Therefore, it is still necessary to improve the formaldehyde sensing device.

SUMMARY OF THE INVENTION

Accordingly, one objective of the present invention is to provide a self-powered formaldehyde sensing device, which utilizes the self-powered ability to perform formaldehyde sensing.

In order to overcome the technical problems in prior art, the present invention provides a self-powered formaldehyde sensing device, comprising: a triboelectric material electrode layer including a first substrate and a first electrode layer formed on the first substrate; a triboelectric material dielectric layer including a second substrate, a second electrode layer formed on the second substrate, a dielectric reacting layer formed on the second electrode layer, and a reaction modification layer formed on the dielectric reacting layer to surface-modify the dielectric reacting layer, the reaction modification layer being a phosphomolybdic acid complex (cPMA) layer, the phosphomolybdic acid complex of the phosphomolybdic acid complex layer being obtained by dissolving 4,4'-bipyridine (BPY) in isopropanol (IPA) and then mixing with phosphomolybdic acid (PMA) solution; an elastic spacer being disposed between the triboelectric material electrode layer and the triboelectric material dielectric layer so that the triboelectric material electrode layer and the triboelectric material dielectric layer are elastically spaced from and facing each other in a manner that the first electrode layer facing the reaction modification layer; and an external circuit being electrically connected between the triboelectric material electrode layer and the triboelectric material dielectric layer, wherein when an airflow-to-be-sensed is applied to the self-powered formaldehyde sensing device, the triboelectric material electrode layer and the triboelectric material dielectric layer are in contact with each other by propulsion of the airflow-to-be-sensed and move away from each other by an elastic restoring force of the elastic spacer, thereby generating a generation current in the external circuit by contact electrification and electrostatic induction between the triboelectric material electrode layer and the triboelectric material dielectric layer, and when the airflow-to-be-sensed contains formaldehyde, an oxidation-reduction reaction between the reaction modification layer and formaldehyde contained in the airflow-to-be-sensed is caused, and a sensing signal current is further generated in the external circuit correspondingly.

In one embodiment of the present invention, the triboelectric material electrode layer and the triboelectric material dielectric layer are flexible structural layers so that the self-powered formaldehyde sensing device is provided as a self-powered flexible formaldehyde sensing device.

In one embodiment of the present invention, the first substrate and the second substrate are polyethylene naphthalate (PEN) substrates.

In one embodiment of the present invention, the dielectric reacting layer is a polydimethylsiloxane (PDMS) layer.

In one embodiment of the present invention, the triboelectric material electrode layer further includes a surface modification layer formed on the first electrode layer to surface modify the first electrode layer.

In one embodiment of the present invention, the first electrode layer is a silver nanoparticle electrode layer, the surface modification layer is a phenothiazine (PTZ) layer.

In one embodiment of the present invention, the second electrode layer is a poly(3,4-ethylenedioxythiophene):poly(styrenesulfonate) (PEDOT:PSS) electrode layer.

In one embodiment of the present invention, the second electrode layer is an indium tin oxide (ITO) electrode layer.

In one embodiment of the present invention, comprising a formaldehyde concentration calculation module, which is electrically connected to the external circuit to calculate the formaldehyde concentration according to the sensing signal current, thereby generating a formaldehyde concentration sensing result.

In one embodiment of the present invention, the formaldehyde concentration calculation module further includes a wireless network transmission unit for uploading the formaldehyde concentration sensing result to a cloud health monitoring system.

Since the self-powered formaldehyde sensing device of the present invention has the characteristics of self-powered ability, fast response time, and can be operated at room temperature, the user can quickly obtain the formaldehyde sensing results. In addition, component materials used in the self-powered formaldehyde sensing device not only provide the self-powered formaldehyde sensing device with good stability and water resistance, but also allow the self-powered formaldehyde sensing device to return to its pre-sensing state without complicated cleaning procedures after the formaldehyde has been sensed, thereby allowing it to be reused.

DETAILED DESCRIPTION OF THE PREFERRED EMBODIMENTS

The preferred embodiments of the present invention are described in detail below with reference to FIG. 1 to FIG. 8b. The description is used for explaining the embodiments of the present invention only, but not for limiting the scope of the claims.

Figure 1:
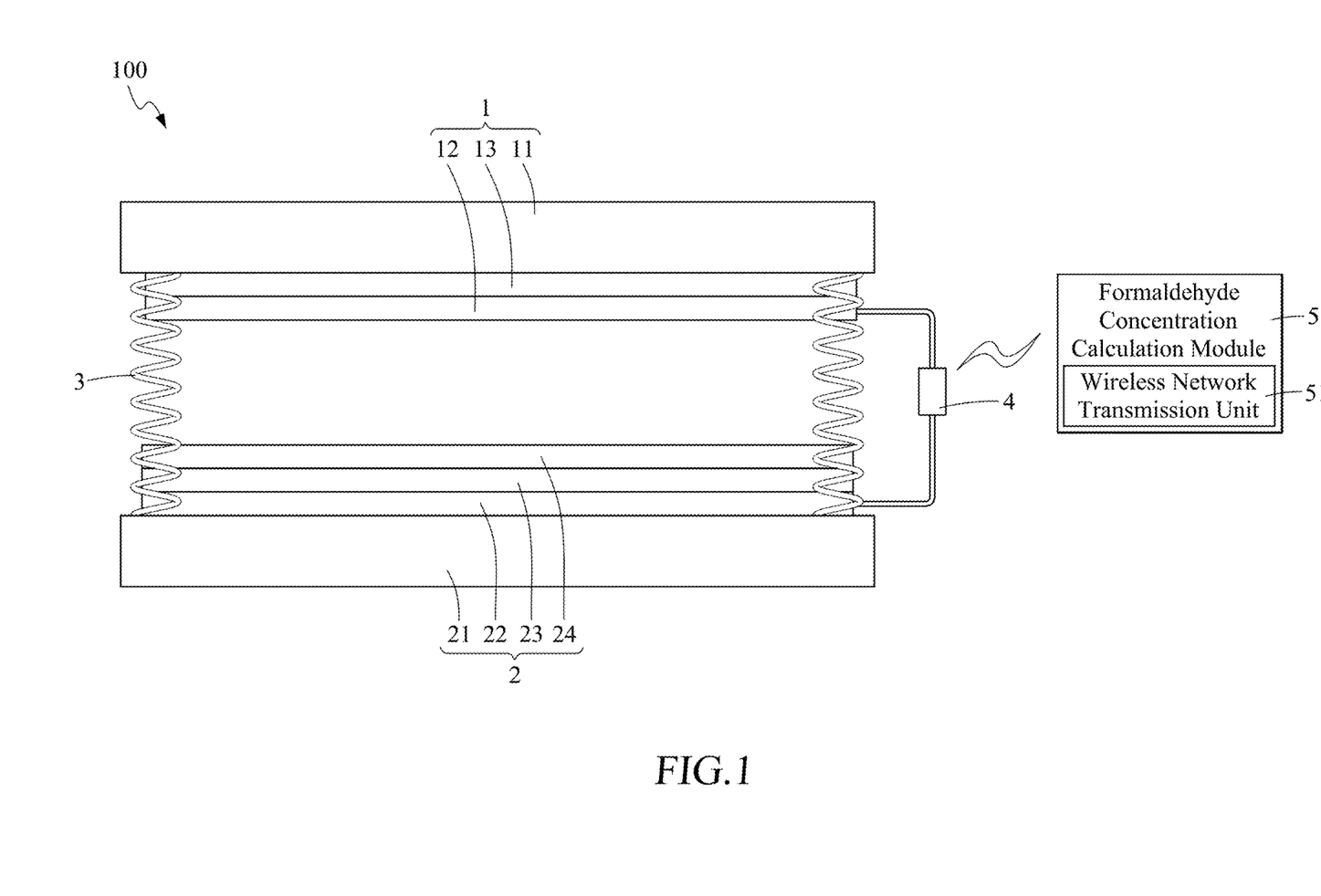
FIG. 1 is a schematic view illustrating a self-powered formaldehyde sensing device according to one embodiment of the present invention.

As shown in FIG. 1, a self-powered formaldehyde sensing device 100 according to an embodiment of the present invention comprises: a triboelectric material electrode layer 1 including a first substrate 11 and a first electrode layer 12 formed on the first substrate 11; a triboelectric material dielectric layer 2 including a second substrate 21, a second electrode layer 22 formed on the second substrate 21, a dielectric reacting layer 23 formed on the second electrode layer 22, and a reaction modification layer 24 formed on the dielectric reacting layer 23 to surface-modify the dielectric reacting layer 23, the reaction modification layer 24 being a phosphomolybdic acid complex (cPMA) layer, the phosphomolybdic acid complex of the phosphomolybdic acid complex layer being obtained by dissolving 4,4'-bipyridine (BPY) in isopropanol (IPA) and then mixing with phosphomolybdic acid (PMA) solution; an elastic spacer 3 being disposed between the triboelectric material electrode layer 1 and the triboelectric material dielectric layer 2 so that the triboelectric material electrode layer 1 and the triboelectric material dielectric layer 2 are elastically spaced from and facing each other in a manner that the first electrode layer 12 facing the reaction modification layer 24; and an external circuit 4 being electrically connected between the triboelectric material electrode layer 1 and the triboelectric material dielectric layer 2, wherein when an airflow-to-be-sensed is applied to the self-powered formaldehyde sensing device 100, the triboelectric material electrode layer 1 and the triboelectric material dielectric layer 2 are in contact with each other by propulsion of the airflow-to-be-sensed and move away from each other by an elastic restoring force of the elastic spacer 3, thereby generating a generation current in the external circuit 4 by contact electrification and electrostatic induction between the triboelectric material electrode layer 1 and the triboelectric material dielectric layer 2, and when the airflow-to-be-sensed contains formaldehyde, an oxidation-reduction reaction between the reaction modification layer and formaldehyde contained in the airflow-to-be-sensed is caused, and a sensing signal current is further generated in the external circuit 4 correspondingly.

Specifically, the present invention is to apply a triboelectric nanogenerator (TENG) to gas (i.e., formaldehyde) sensing devices. The TENG utilizes contact electrification and electrostatic induction to convert mechanical energy into electrical energy. The working principle of TENG is that when two triboelectric materials come into contact, due to the difference in electron affinity (EA), electron transfer occurs at the interface, and as the distance between the two triboelectric materials varies, the electrostatic induction charge varies, and electrons flow through the external circuit to correspondingly generate a current output.

The present invention uses cPMA obtained by mixing PMA with BPY as the reaction modification layer 24 for surface-modifying the dielectric reacting layer 23. On the one hand, the multi-negative charge structure of cPMA itself generates a dipole on the surface of the dielectric reacting layer 23 to achieve the effect of modifying the work function (WF); on the other hand, formaldehyde gas sensing is performed by the characteristic of PMA molecules that can easily capture electrons.

Figure 2:
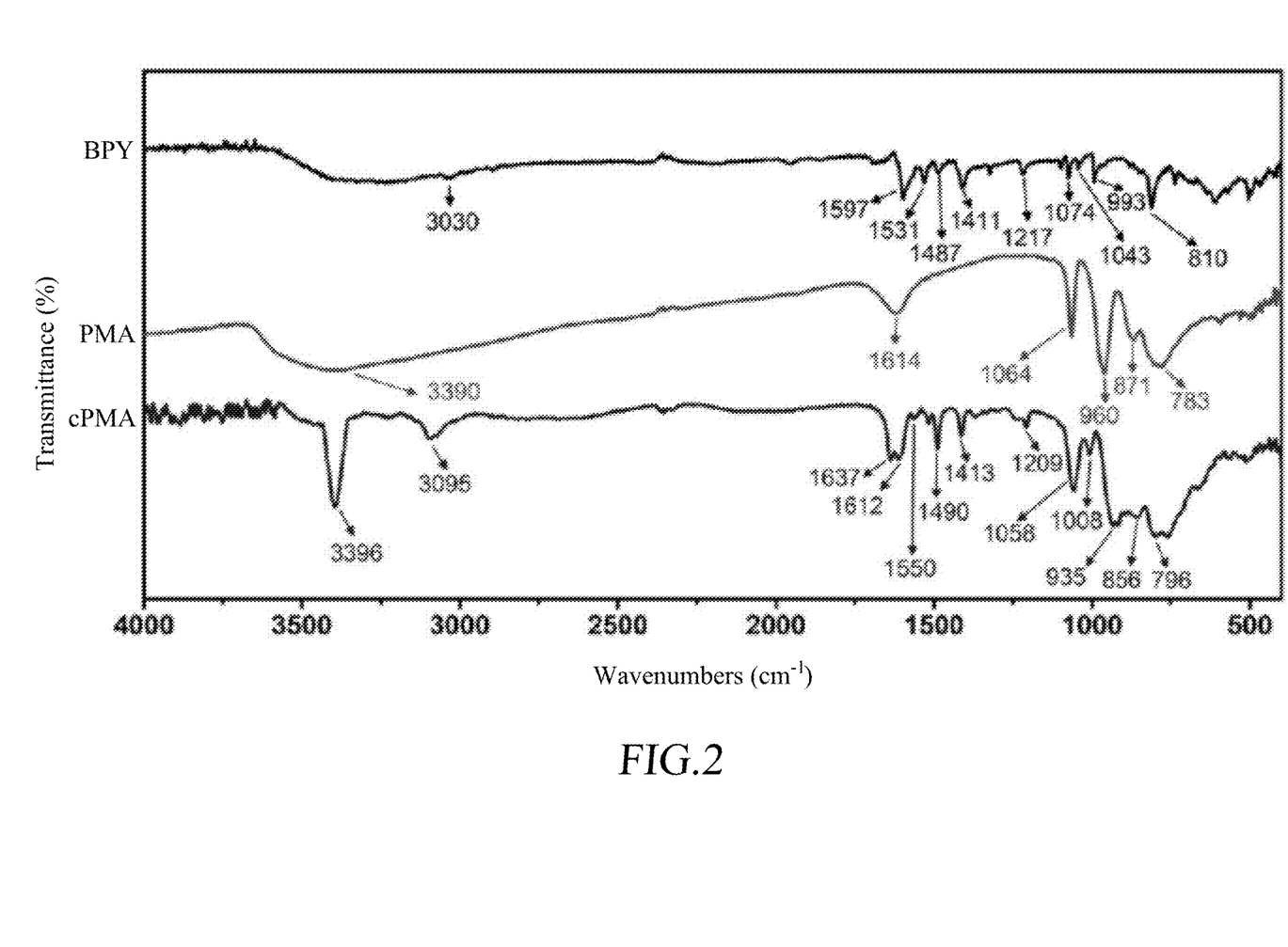
FIG. 2 is a Fourier-transform infrared spectroscopy (FTIR) spectra of cPMA of the self-powered formaldehyde sensing device according to the embodiment of the present invention.

The cPMA of the present invention does not absorb water in the atmosphere and has thermal stability so that the self-powered formaldehyde sensing device 100 of the present invention can be used in a high-humidity environment for long periods of time. As shown in FIG. 2, the embodiment of the present invention uses Fourier-transform infrared spectroscopy (FTIR) technology to analyze the molecular structure of cPMA to prove that cPMA retains the characteristic signals of the main functional groups of both PMA and BPY.

Specifically, when the self-powered formaldehyde sensing device 100 senses formaldehyde, the formaldehyde will be absorbed onto the reaction modification layer 24, and an oxidation-reduction reaction will be caused between the reaction modification layer 24 and formaldehyde contained in the airflow-to-be-sensed, thereby generating excess electrons on the surface of the reaction modification layer 24. The triboelectrification of the self-powered formaldehyde sensing device 100 will be shielded by these excess electrons, resulting in a voltage drop. The generation current and the correspondingly generated sensing signal current are the electrical performance outputs of the self-powered formaldehyde sensing device 100.

Figure 3A:
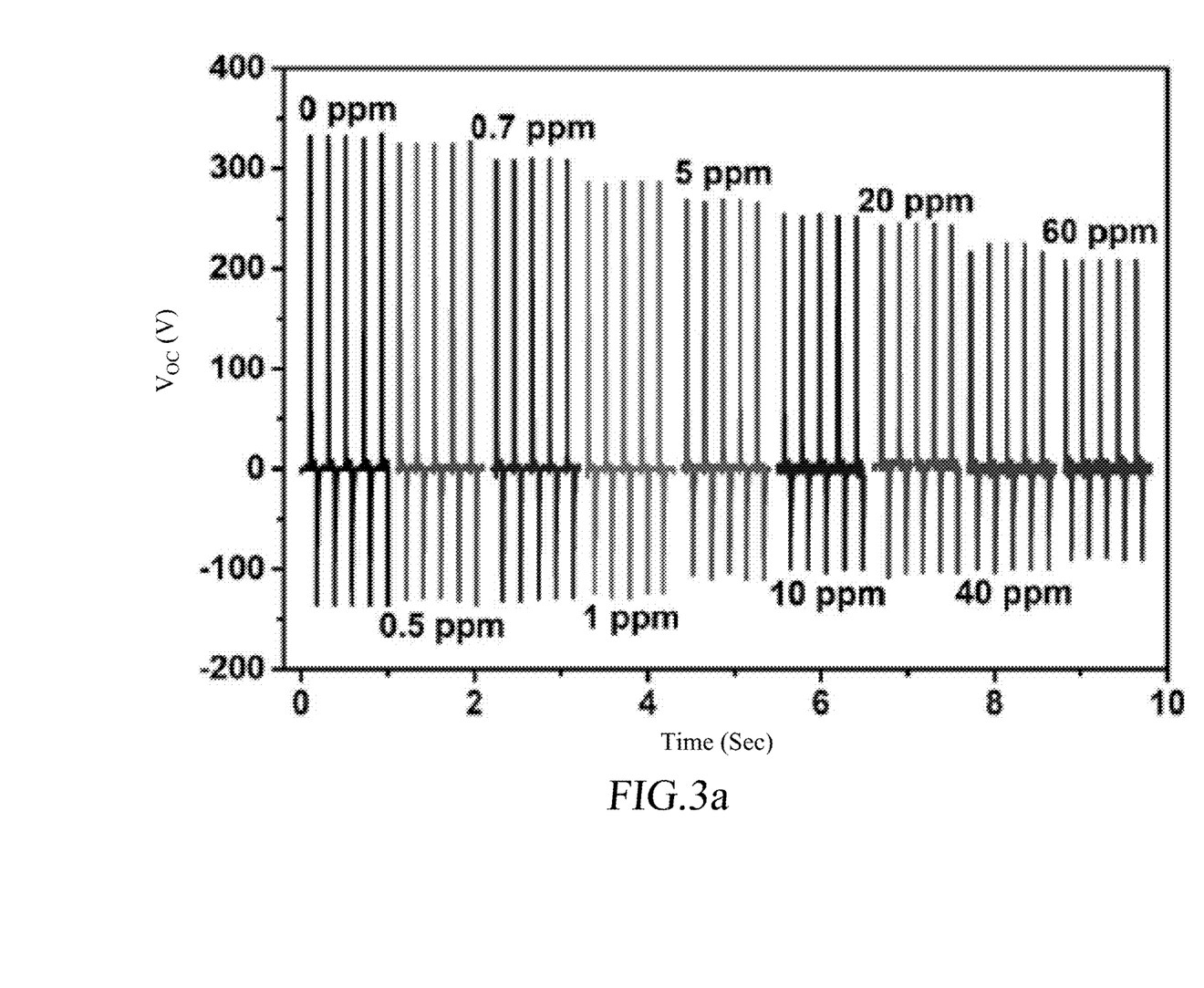
FIG. 3a is a schematic view illustrating electrical performance outputs presented by the self-powered formaldehyde sensing device according to the embodiment of the present invention when exposed to different concentrations of formaldehyde.
Figure 3B:
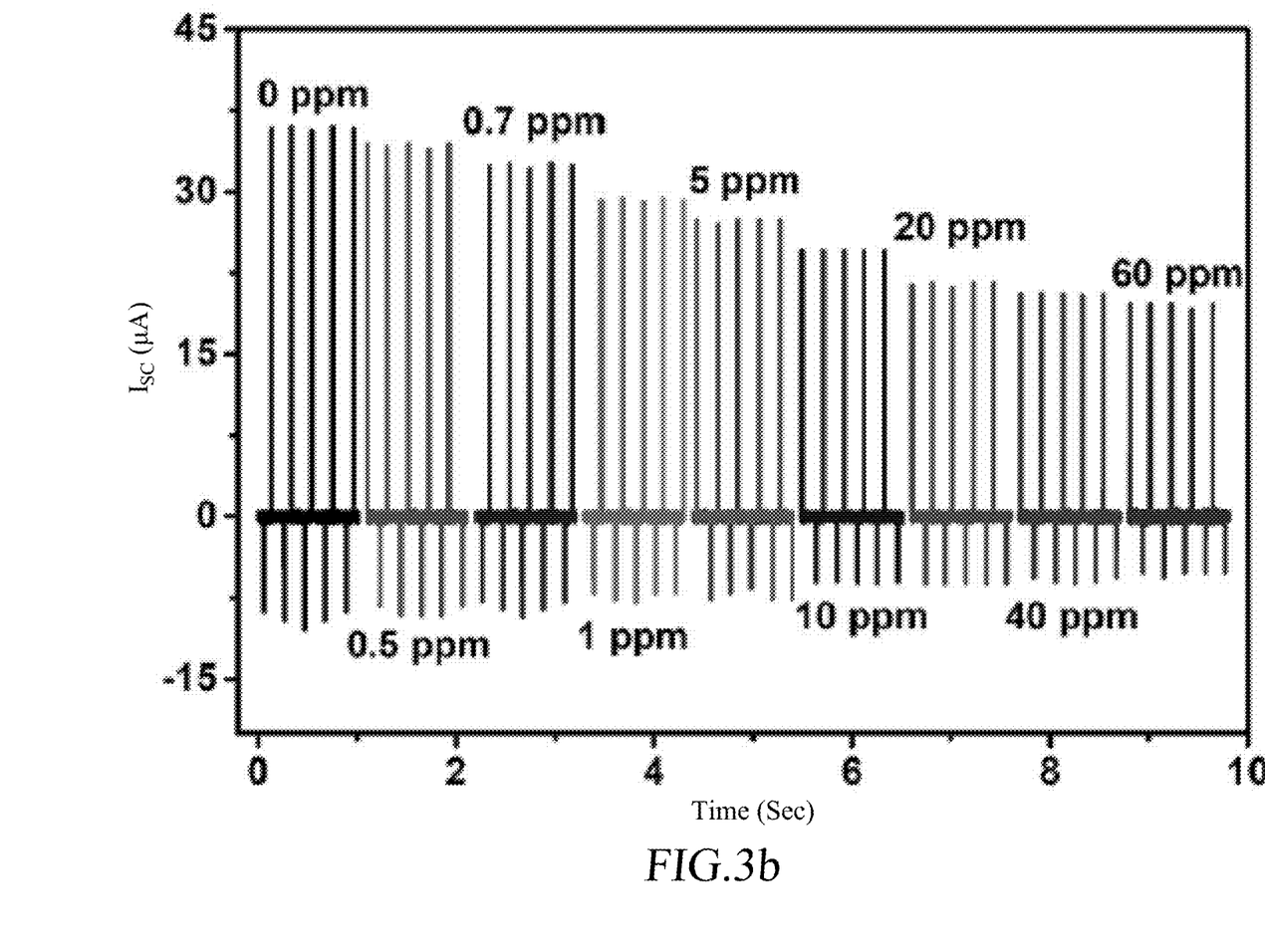
FIG. 3b is a schematic view illustrating electrical performance outputs presented by the self-powered formaldehyde sensing device according to the embodiment of the present invention when exposed to different concentrations of formaldehyde.

Furthermore, as shown in FIG. 3a and FIG. 3b, "$V_{oc}$" in the figures represents the open-circuit voltage, and "$I_{sc}$" in the figures represents the short-circuit current. In the embodiment of the present invention, the self-powered formaldehyde sensing device 100 is exposed to formaldehyde environments with different concentrations, wherein the formaldehyde concentrations are 0.5 ppm, 0.7 ppm, 1 ppm, 5 ppm, 10 ppm, 20 ppm, 40 ppm, and 60 ppm, respectively, and the self-powered formaldehyde sensing device 100 is placed in the environments for 5 minutes and then taken out to measure the electrical performance output. The figures show that as the formaldehyde concentration increases, the electrical performance outputs (i.e., voltage and current) of the self-powered formaldehyde sensing device 100 decreases. In other words, the sensed concentration of formaldehyde will be inversely proportional to the electrical performance outputs of the self-powered formaldehyde sensing device 100. The reason for this is that since the characteristics of the reaction modification layer 24 change with different concentrations of formaldehyde, the electrical performance outputs (including voltage and current) of the self-powered formaldehyde sensing device 100 will also change with different concentrations of formaldehyde. Specifically, when formaldehyde is sensed by the self-powered formaldehyde sensing device 100, the electron affinity of the PMA molecule decreases due to the gain of electrons of the PMA in the reaction modification layer 24, thus reducing the number of electrons transferred from the electrode. The figure also shows that the minimum sensing limit of the self-powered formaldehyde sensing device 100 can reach 0.5 ppm, and a good response can also be maintained at 60 ppm.

Response is the basis for judging the sensitivity of a TENG sensing device. The calculation formula of response is as follow:

$$\text{Response} = \frac{V_a - V_g}{V_a}, \text{ and/or Response} = \frac{I_a - I_g}{I_a},$$

wherein "$V_a$" represents the initial voltage value before sensing, "$V_g$" represents the voltage value measured by the TENG sensing device when exposed to the target gas, "$I_a$" represents the initial current value before sensing, "$I_g$" represents the current value measured by the TENG sensing device when exposed to the target gas, the response is used as a criterion for judging the merit of the TENG sensing device. Furthermore, if a TENG sensing device has a particularly high response to a certain specific kind of gas among a variety of gases, it means that the TENG sensing device has gas sensing specificity and high sensitivity to that specific kind of gas.

Figure 4:
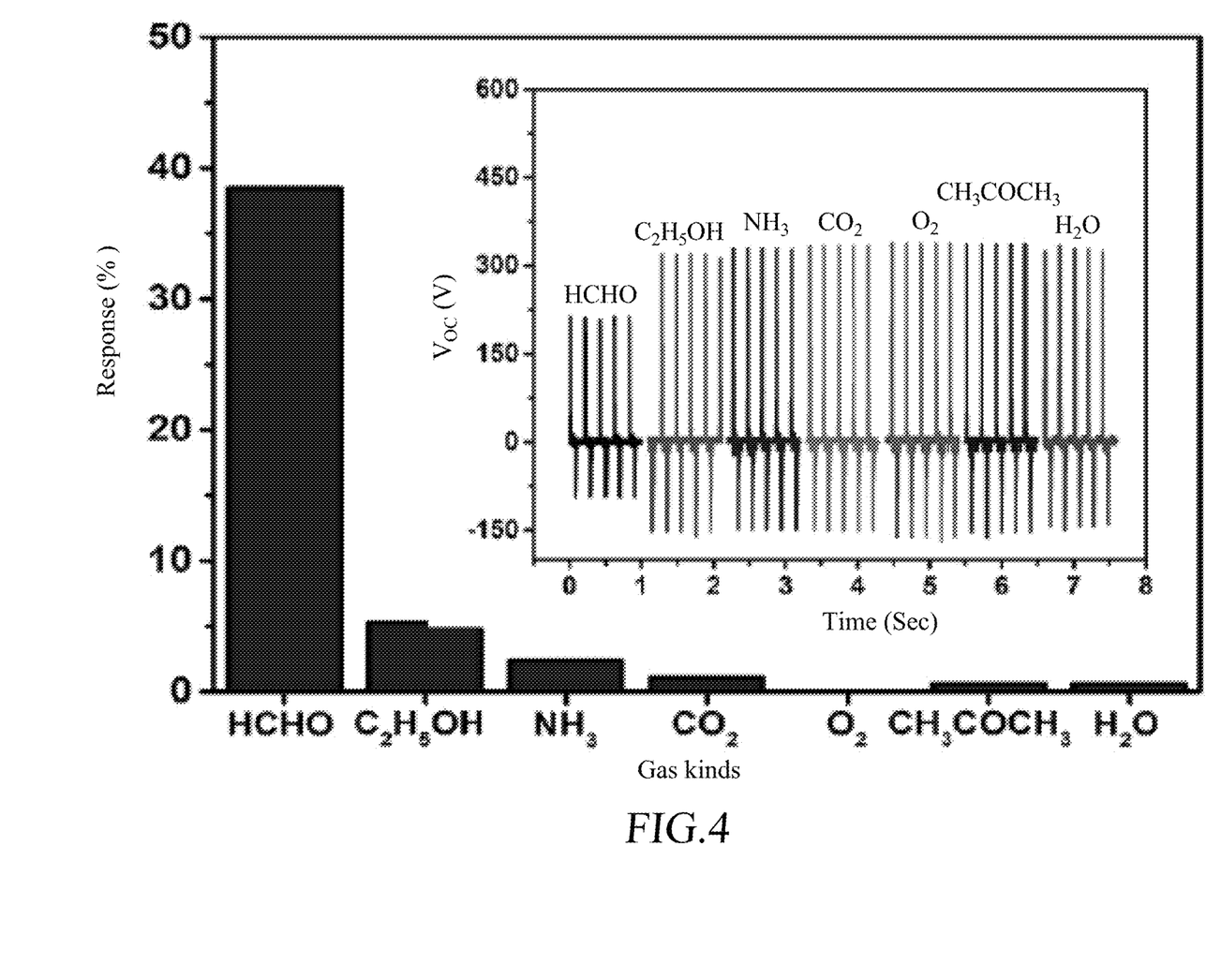
FIG. 4 is a schematic view illustrating the response of the self-powered formaldehyde sensing device according to the embodiment of the present invention when sensing different kinds of gases.

As shown in FIG. 4, the self-powered formaldehyde sensing device 100 of the present invention has a significantly higher response to formaldehyde (the chemical formula is HCHO) than other kinds of gases. "$V_{oc}$" in the figure represents the open-circuit voltage, which is the electrical performance output of the self-powered formaldehyde sensing device 100. The figure shows that when formaldehyde is sensed by the self-powered formaldehyde sensing device 100, the $V_{oc}$ exhibited by the self-powered formaldehyde sensing device 100 is significantly lower than the exhibited $V_{oc}$ when other kinds of gases are sensed. The above results show that the self-powered formaldehyde sensing device 100 of the present invention indeed has gas sensing specificity and high sensitivity to formaldehyde.

Figure 5A:
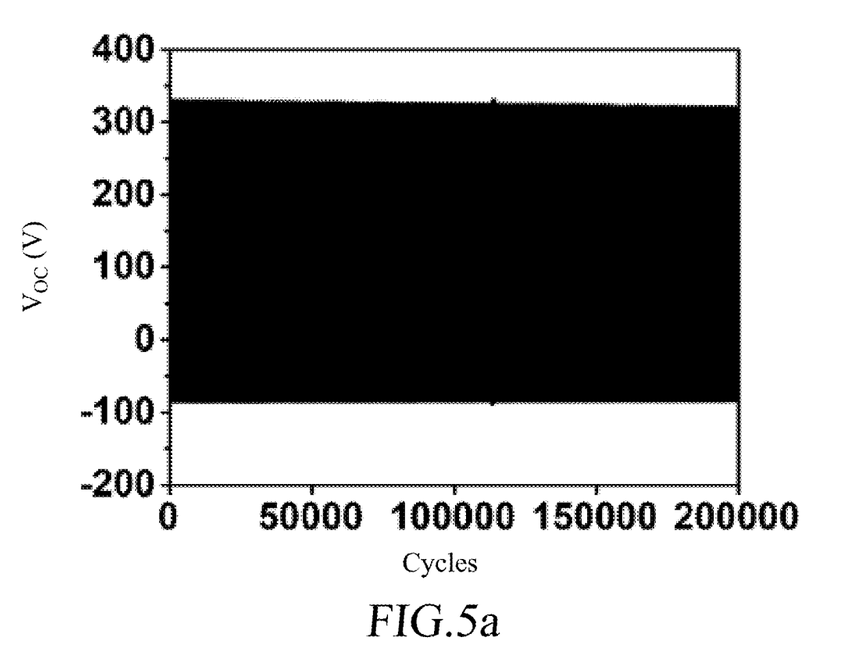
FIG. 5a is a schematic view illustrating a stability test result of the self-powered formaldehyde sensing device according to the embodiment of the present invention.
Figure 5B:
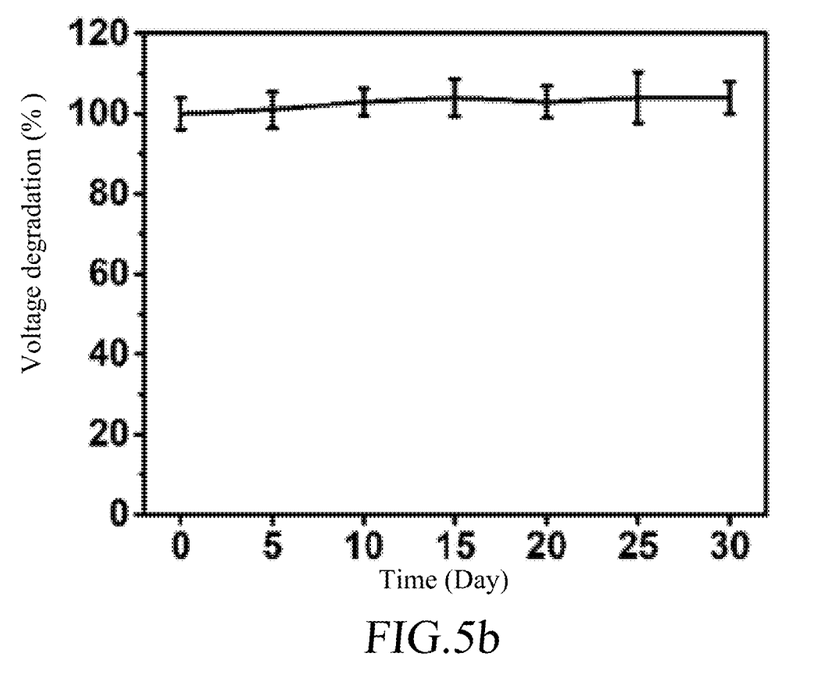
FIG. 5b is a schematic view illustrating a stability test result of the self-powered formaldehyde sensing device according to the embodiment of the present invention.
Figure 5C:
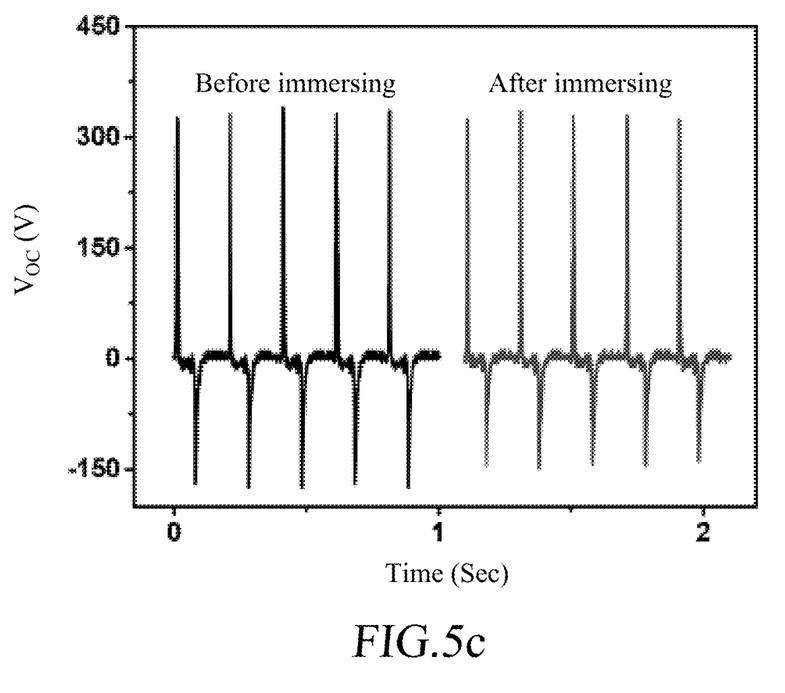
FIG. 5c is a schematic view illustrating a stability test result of the self-powered formaldehyde sensing device according to the embodiment of the present invention.

As shown in FIG. 5a, the self-powered formaldehyde sensing device 100 of the present invention is tested under 200000 cycles, i.e., the triboelectric material electrode layer 1 and the triboelectric material dielectric layer 2 are in a state of continuous contact with each other then move away from each other under 200000 cycles for a long period of time (ambient conditions of 25±2° C. and 65±5% relative humidity (RH)), and the measured $V_{oc}$ value has almost no decrease. thus demonstrating that the self-powered formaldehyde sensing device 100 of the present invention can be used for a long time and will not be damaged due to frequent use. On the other hand, as shown in FIG. 5b, the self-powered formaldehyde sensing device 100 is placed under the ambient conditions of 25±2° C. and 65±5% RH, and the $V_{oc}$ measurement is performed every 5 days, and the measurement results are almost unchanged after 30 days. As shown in FIG. 5c, the self-powered formaldehyde sensing device 100 is immersed in water and timed, and after 12 hours, the self-powered formaldehyde sensing device 100 is taken out and blown dry with $N_2$ gas. Next, the $V_{oc}$ measurement is performed, the measurement results show that the difference between pre-immersed and post-immersed $V_{oc}$ values is very small and can be considered as no decrease in the measured $V_{oc}$ value. The above results all show that the self-powered formaldehyde sensing device 100 of the present invention has excellent stability.

Figure 6:
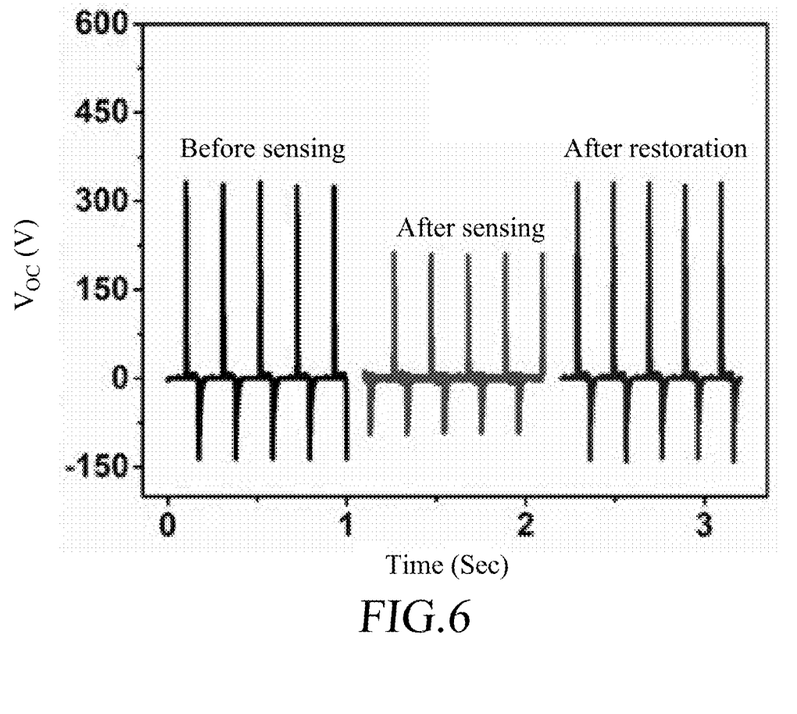
FIG. 6 is a schematic view illustrating a performance recovery test result of the self-powered formaldehyde sensing device according to the embodiment of the present invention.

As shown in FIG. 6, in the self-powered formaldehyde sensing device 100 of the present invention, by immersing the self-powered formaldehyde sensing device 100, which has performed formaldehyde sensing, in hot water in the temperature range of 90° C. to 100° C. for 5 to 15 minutes, the electrical performance output of the self-powered formaldehyde sensing device 100 is restored to its pre-sensing state (i.e., the self-powered formaldehyde sensing device 100 is restored to its initial performance). In other words, the self-powered formaldehyde sensing device 100 of the present invention is reusable, and the recovery method is simple and time-saving.

Figure 7:
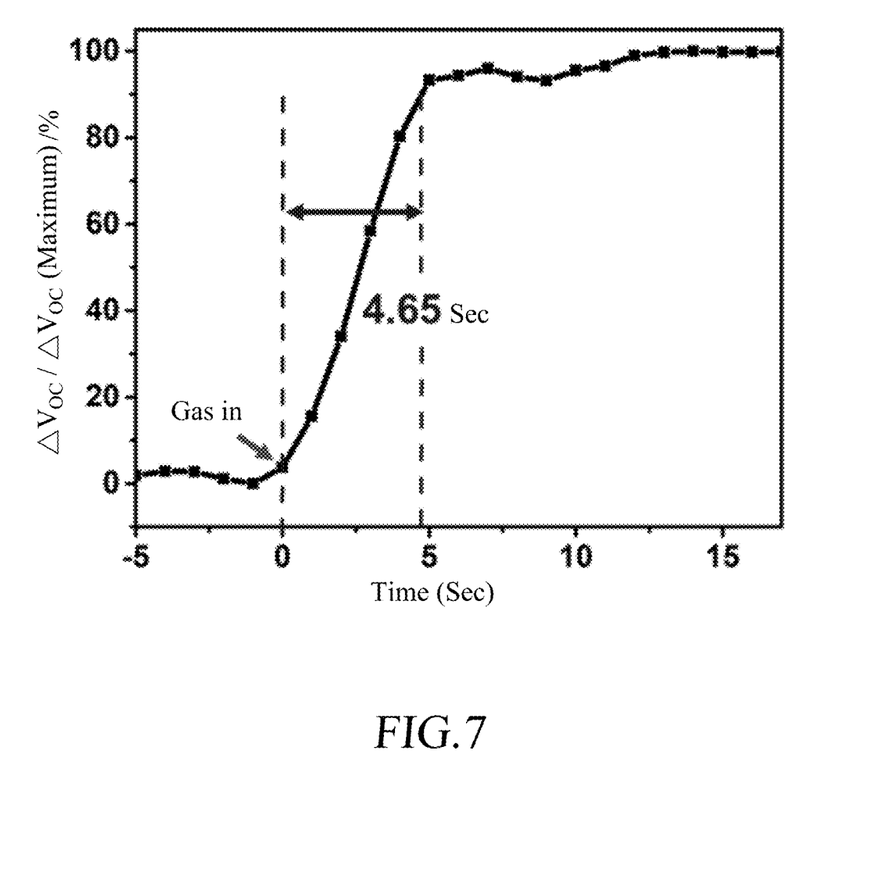
FIG. 7 is a schematic view illustrating the response time of the self-powered formaldehyde sensing device according to the embodiment of the present invention.

As shown in FIG. 7, the response time is the time required for a sensing device to sense a target gas until a certain change in its electrical performance output occurs. The figure shows that the time required for the self-powered formaldehyde sensing device 100 of the present invention to sense formaldehyde until a 90% change in electrical performance output is only 4.65 seconds, showing that the self-powered formaldehyde sensing device 100 of the present invention has a fast response time, wherein the $0^{th}$ second is the time point when formaldehyde gas is introduced.

As shown in FIG. 1, in the self-powered formaldehyde sensing device 100 according to the embodiment of the present invention, the triboelectric material electrode layer 1 and the triboelectric material dielectric layer 2 are flexible structural layers so that the self-powered formaldehyde sensing device 100 is provided as a self-powered flexible formaldehyde sensing device.

Figure 8A:
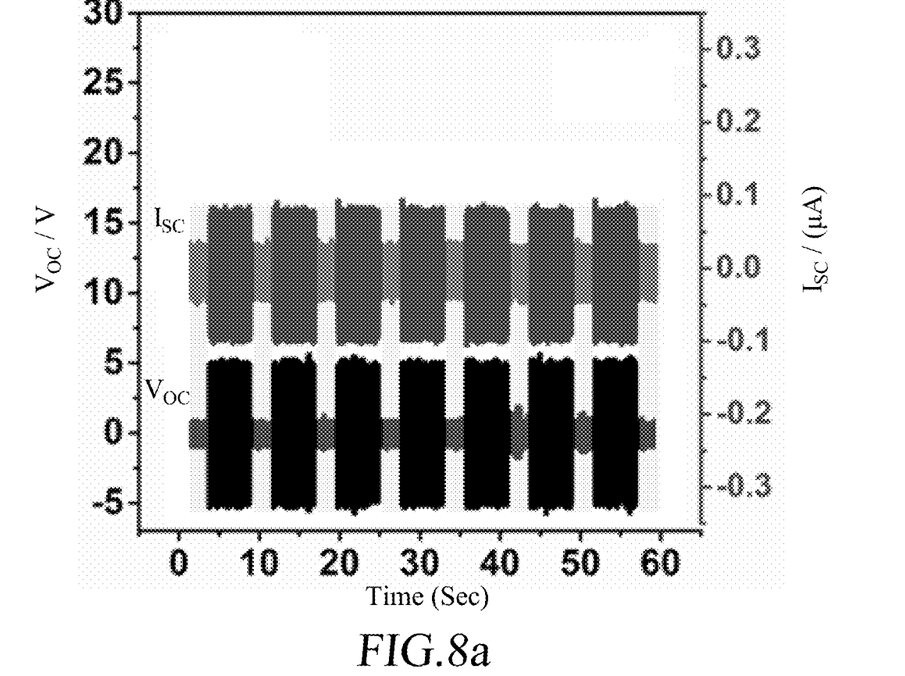
FIG. 8a is a schematic view illustrating a test result of the self-powered formaldehyde sensing device according to the embodiment of the present invention applied to a mask.
Figure 8B:
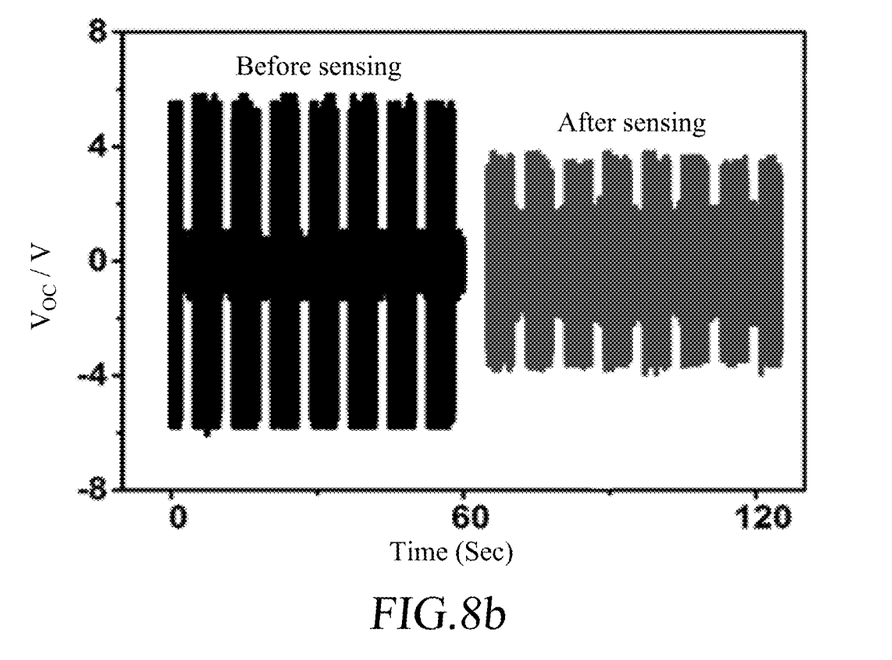
FIG. 8b is a schematic view illustrating a test result of the self-powered formaldehyde sensing device according to the embodiment of the present invention applied to a mask.

Specifically, since a flexible material is provided as the component material used in the self-powered formaldehyde sensing device 100 of the present invention, the self-powered formaldehyde sensing device 100 can be applied to a wider range of applications. Furthermore, the self-powered formaldehyde sensing device 100 of the present invention can be applied to wearable electronic devices, such as a mask-type self-powered formaldehyde sensing device 100. As shown in FIG. 8a, the self-powered formaldehyde sensing device 100 can still be driven by airflow when applied to a mask; and as shown in FIG. 8b, the self-powered formaldehyde sensing device 100 is applied to a mask, and the electrical performance outputs obtained after sensing formaldehyde is significantly reduced, which means that the self-powered formaldehyde sensing device 100 is highly feasible to be applied to the mask.

In the self-powered formaldehyde sensing device 100 according to the embodiment of the present invention, the first substrate 11 and the second substrate 21 are polyethylene naphthalate (PEN) substrates.

In the self-powered formaldehyde sensing device 100 according to the embodiment of the present invention, the dielectric reacting layer is a polydimethylsiloxane (PDMS) layer.

As shown in FIG. 1, in the self-powered formaldehyde sensing device 100 according to the embodiment of the present invention, the triboelectric material electrode layer 1 further includes a surface modification layer 13 formed on the first electrode layer 12 to surface-modify the first electrode layer 12.

In the self-powered formaldehyde sensing device 100 according to the embodiment of the present invention, the first electrode layer 12 is a silver nanoparticle electrode layer, the surface modification layer 13 is a phenothiazine (PTZ) layer.

Specifically, the first electrode layer 12 is the silver nanoparticle electrode layer in a solution state. The present invention uses PTZ as the surface modification layer 13 for surface-modifying the silver nanoparticle electrode layer, where PTZ has the functions of electrode modification and nucleation induction. Furthermore, PTZ can promote the film formation of silver nanoparticles to improve the film conductivity of silver nanoparticles, and it can also modify the WF of silver nanoparticles to improve the electron transfer effect, thereby improving the electrical performance output of the electrode.

The manufacturing process of the self-powered formaldehyde sensing device 100 of the present invention is a solution-based process and can therefore be produced in large volumes, which not only has a simple process and high product yield, but also has a low manufacturing cost compared to the conventional technology.

In the self-powered formaldehyde sensing device 100 according to the embodiment of the present invention, the second electrode layer 22 is a poly(3,4-ethylenedioxythiophene):poly(styrenesulfonate) (PEDOT:PSS) electrode layer.

Specifically, the second electrode layer 22 is an electrode layer composed of PEDOT:PSS which is a flexible conductive material. In addition, the flexible conductive material used in the second electrode layer 22 of the present invention is not limited to this, the second electrode layer 22 can also be an electrode layer composed of other kinds of flexible conductive materials, such as a conductive polymer film electrode layer.

In the self-powered formaldehyde sensing device 100 according to the embodiment of the present invention, the second electrode layer 22 is an indium tin oxide (ITO) electrode layer.

Specifically, the second electrode layer 22 can also be an electrode layer composed of ITO, which is an inflexible conductive material. In addition, the inflexible conductive material used in the second electrode layer 22 of the present invention is not limited to this, the second electrode layer 22 can also be an electrode layer composed of other kinds of inflexible conductive materials, such as a metal thin film electrode layer.

Furthermore, in the case that the second electrode layer 22 is an electrode layer composed of an inflexible conductive material, the second electrode layer 22 also has the function of the second substrate 21.

As shown in FIG. 1, the self-powered formaldehyde sensing device 100 according to the embodiment of the present invention further comprises a formaldehyde concentration calculation module 5, which is electrically connected to the external circuit 4 to calculate the formaldehyde concentration according to the sensing signal current, thereby generating a formaldehyde concentration sensing result.

As shown in FIG. 1, in the self-powered formaldehyde sensing device 100 according to the embodiment of the present invention, the formaldehyde concentration calculation module 5 further includes a wireless network transmission unit 51 for uploading the formaldehyde concentration sensing result to a cloud health monitoring system.

Specifically, the cloud health monitoring system can be an Internet of Things (IoT).

Furthermore, the formaldehyde concentration sensing result can be uploaded to the cloud health monitoring system for real-time monitoring of the user's own health status through big data analysis and prediction.

With the technical means adopted by the present invention, the self-powered formaldehyde sensing device 100 of the present invention is able to provide formaldehyde gas sensing with high sensitivity and high specificity, not only for breath diagnosis but also for environmental related gas sensing. Since the self-powered formaldehyde sensing device 100 of the present invention has the characteristics of self-powered ability, fast response time, and can be operated at room temperature, the user can quickly obtain the formaldehyde sensing results. In addition, component materials used in the self-powered formaldehyde sensing device 100 not only provide the self-powered formaldehyde sensing device 100 with good stability and water resistance but also allow the self-powered formaldehyde sensing device 100 to return to its pre-sensing state without complicated cleaning procedures after the formaldehyde has been sensed, thereby allowing it to be reused.

On the other hand, component materials used in the self-powered formaldehyde sensing device can be flexible materials so that the self-powered formaldehyde sensing device 100 can be used in a wider range of applications and to assist users in monitoring their own health through the cloud health monitoring system such as the IoT.

The above description is only an explanation of the preferred embodiments of the present invention. One having ordinary skill in the art can make various modifications according to the above description and the claims defined below. However, those modifications shall still fall within the scope of the present invention.

What is claimed is:

1. A self-powered formaldehyde sensing device, comprising:
   a triboelectric material electrode layer including a first substrate and a first electrode layer formed on the first substrate;
   a triboelectric material dielectric layer including a second substrate, a second electrode layer formed on the second substrate, a dielectric reacting layer formed on the second electrode layer, and a reaction modification layer formed on the dielectric reacting layer to surface-modify the dielectric reacting layer, the reaction modification layer being a phosphomolybdic acid complex (cPMA) layer, the phosphomolybdic acid complex of the phosphomolybdic acid complex layer being obtained by dissolving 4,4'-bipyridine (BPY) in isopropanol (IPA) and then mixing with phosphomolybdic acid (PMA) solution;

an elastic spacer being disposed between the triboelectric material electrode layer and the triboelectric material dielectric layer so that the triboelectric material electrode layer and the triboelectric material dielectric layer are elastically spaced from and facing each other in a manner that the first electrode layer is facing the reaction modification layer; and an external circuit being electrically connected between the triboelectric material electrode layer and the triboelectric material dielectric layer, wherein, when an airflow-to-be-sensed is applied to the self-powered formaldehyde sensing device, the triboelectric material electrode layer and the triboelectric material dielectric layer are in contact with each other by propulsion of the airflow-to-be-sensed and move away from each other by an elastic restoring force of the elastic spacer, thereby generating a generation current in the external circuit by contact electrification and electrostatic induction between the triboelectric material electrode layer and the triboelectric material dielectric layer, and when the airflow-to-be-sensed contains formaldehyde, an oxidation-reduction reaction between the reaction modification layer and formaldehyde contained in the airflow-to-be-sensed is caused, and a sensing signal current is further generated in the external circuit correspondingly.

2. The self-powered formaldehyde sensing device as claimed in claim 1, wherein the triboelectric material electrode layer and the triboelectric material dielectric layer are flexible structural layers so that the self-powered formaldehyde sensing device is provided as a self-powered flexible formaldehyde sensing device.

3. The self-powered formaldehyde sensing device as claimed in claim 2, wherein the first substrate and the second substrate are polyethylene naphthalate (PEN) substrates.

4. The self-powered formaldehyde sensing device as claimed in claim 1, wherein the dielectric reacting layer is a polydimethylsiloxane (PDMS) layer.

5. The self-powered formaldehyde sensing device as claimed in claim 1, wherein the triboelectric material electrode layer further includes a surface modification layer formed on the first electrode layer to surface modify the first electrode layer.

6. The self-powered formaldehyde sensing device as claimed in claim 4, wherein the triboelectric material electrode layer further includes a surface modification layer formed on the first electrode layer to surface modify the first electrode layer.

7. The self-powered formaldehyde sensing device as claimed in claim 5, wherein the first electrode layer is a silver nanoparticle electrode layer and the surface modification layer is a phenothiazine (PTZ) layer.

8. The self-powered formaldehyde sensing device as claimed in claim 6, wherein the first electrode layer is a silver nanoparticle electrode layer and the surface modification layer is a phenothiazine (PTZ) layer.

9. The self-powered formaldehyde sensing device as claimed in claim 1, wherein the second electrode layer is a poly(3,4-ethylenedioxythiophene):poly(styrenesulfonate) (PEDOT:PSS) electrode layer.

10. The self-powered formaldehyde sensing device as claimed in claim 1, wherein the second electrode layer is an indium tin oxide (ITO) electrode layer.

11. The self-powered formaldehyde sensing device as claimed in claim 1, further comprising a formaldehyde concentration calculation module, which is electrically connected to the external circuit to calculate the formaldehyde concentration according to the sensing signal current, thereby generating a formaldehyde concentration sensing result.

12. The self-powered formaldehyde sensing device as claimed in claim 11, wherein the formaldehyde concentration calculation module further includes a wireless network transmission unit for uploading the formaldehyde concentration sensing result to a cloud health monitoring system.

* * * * *